United States Patent [19]

Rosenwald

[11] Patent Number: 4,484,922
[45] Date of Patent: Nov. 27, 1984

[54] OCCULAR DEVICE

[76] Inventor: Peter L. Rosenwald, 38 Currier Way, Cheshire, Conn. 06410

[21] Appl. No.: 277,188

[22] Filed: Jun. 25, 1981

[51] Int. Cl.³ ............................................. A61K 27/12
[52] U.S. Cl. ............................................. 604/893
[58] Field of Search ................... 128/260; 604/890–900

[56] References Cited

U.S. PATENT DOCUMENTS 3,995,635  12/1976  Higuchi et al. ........................ 128/260

Primary Examiner—Benjamin R. Padgett
Assistant Examiner—T. J. Wallen
Attorney, Agent, or Firm—Mattern, Ware, Stoltz & Fressola

[57] ABSTRACT

An ophthalmic delivery vehicle for dispensing therapeutic medications in the eye is comprised of a body defining a reservoir in which a therapeutic medication is stored and having a semipermeable skin or outer surface through which the medication is dispensed. The body has a frustospherical annular shape and has a size permitting the body to be inserted in the eye in circumscribing relationship with the corneal-scleral junction without intruding upon the junction. In the eye, the annular body extends in the posterior direction over the globe of the eye and into the upper and lower conjunctival sacs behind the upper and lower eyelids.

3 Claims, 4 Drawing Figures

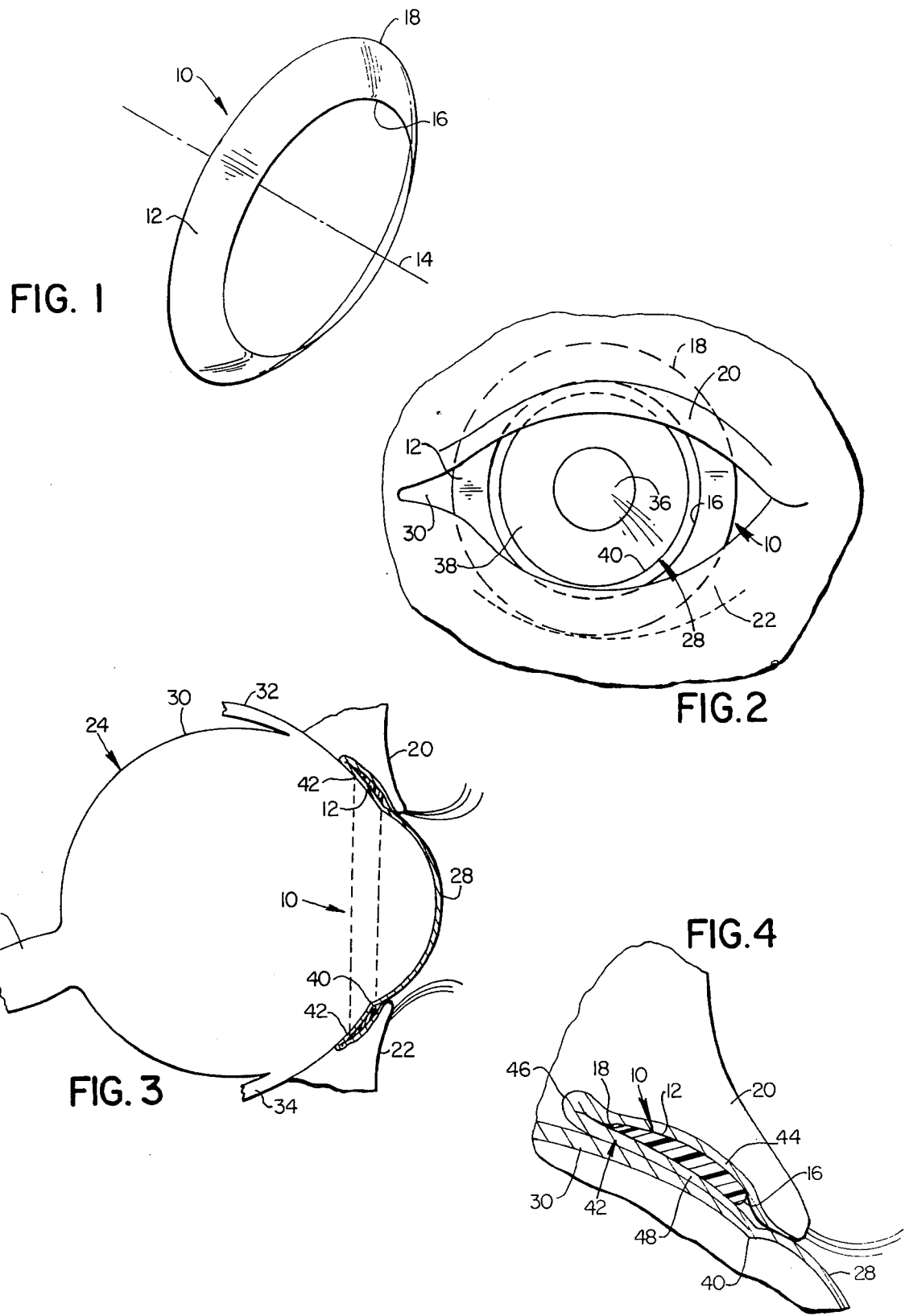

OCCULAR DEVICE

BACKGROUND OF THE INVENTION

The present invention relates to a delivery vehicle for dispensing therapeutic drugs and other medications in the eye. More particularly, the invention relates to a delivery vehicle which may be inserted in the eye for dispensing medication in the eye at a controlled rate over an extended period of time.

Treatment of both temporary and more permanent disorders of the eye has long been accomplished by placing liquids, salves, or other medicaments directly in the eye by means of a squeeze tube or an eye dropper or by flushing the eye with a wash glass. More recently, however, delivery vehicles have been developed in which medication is confined within a small semipermeable body which is inserted under one of the eyelids. The medication is diffused from the body into the tear or lacrimal fluids in the eye and is dispersed over portions of the eye and surrounding areas by the lacrimal fluids.

One form of delivery vehicle inserted into the eye is known as a "soft contact lens". Soft contact lenses consist of a highly porous plastic which can absorb water or other fluids up to 55 per cent of its volume. By soaking such a lens in a fluid medication and inserting the lens in the eye in conventional fashion, a dosage of the medication is distributed in the eye by the lacrimal fluids.

Certain difficulties arise with treatment by means of soft contact lenses. While they absorb a substantial quantity of medication, the plastic material of which they are comprised cannot control the release rate of the medication and as a consequence, strong doses of the medication are dispensed in the eye initially and weak doses after a protracted period. Such variations in the dispensing rate resemble the treatment obtained by periodic applications of medication from an eye dropper and is not the most effective method of treating chronic or more persistent disorders such as glaucoma. Initial doses are strong and lose their effectiveness after a certain period of time. The effects of the medication can be extended by increasing the initial concentration of drugs utilized in the medication; however, the danger of irritation from high toxicity limits such an approach. Additionally, a soft contact lens, as any contact lens, blocks the supply of oxygen to the cornea and, hence, continuous use of the lens for periods of more than twenty four hours is not recommended. Interrupting treatment by removing the lens for rest periods aggravates the difficulty of providing a constant level of medication to the eye.

Another type of delivery vehicle which has overcome many of the difficulties associated with soft contact lenses employs a body of polymeric plastic in which a reservoir of medication is held. The polymeric material can be designed to control the release rate of the medication and thus provide a more uniform level of medication within the eye for extended periods of time. U.S. Pat. Nos. 3,618,604 and 3,828,777 issued to Richard A. Ness disclose delivery vehicles of this type in detail. In practice, the body has a small ellipsoid or bean shape and is inserted in the conjunctival sac between the sclera and one of the eyelids. The medication diffuses through the polymeric material to the surface of the device and is spread over the surface of the eyeball by the lacrimal fluids. The great benefit obtained by these devices is the controlled rate at which the medication is released from the device by the polymeric material. The medication reaches the eye at a relatively uniform rate compared with soft contact lenses and the supply of medication in the device is not immediately expended but, instead, is dispensed gradually over a protracted period of time.

One difficulty which arises from all types of devices inserted in the eye is the sensitivity of the eye to foreign bodies which make contact with the eye, especially in the corneal region. A foreign body can become a source of irritation to the patient which renders the use of an insert impractical and offensive unless it is held in an area of low sensitivity. Irritation stimulates defense mechanisms which protect the eye against foreign objects. The lacrimal glands become more active and produce tearing to wash the object from the eye. Even if tearing is unsuccessful in dislodging an insert, the tear fluids act as a diluent to the dispensed medication and also leach further medication from the delivery vehicle. Excess tearing results in overflow of the conjunctival sacs and, as a result, the medication itself is washed out of the eye in tears.

Another reaction of the eye which aggravates the retention problem is the increased eye mobility caused by local irritation. The eyeball tends to move up and down while the lids open and close in order to expel a foreign object. Even if an insert is not expelled from the eye by these reactions, it can be dislodged to a point where it contacts a highly sensitive area, such as the cornea. In most patients, contact with the cornea cannot be tolerated even momentarily and the eye defense mechanisms are brought immediately to a highly activate state which usually results in expulsion.

It is, accordingly, an object of the present invention to provide an ophthalmic delivery vehicle of the type which provides a slow and controlled release of medication over an extended period of time but without foreign-body awareness and retention problems of the prior art.

SUMMARY OF THE INVENTION

The present invention resides in an ophthalmic delivery vehicle for dispensing therapeutic medications to the eye at controlled rates over an extended period of time. For example, the delivery vehicle may be utilized to treat a chronic disease such as glaucoma by dispensing a drug such as pilocarpine at a relatively uniform rate for a period of, for example, one week without replacement.

The delivery vehicle is comprised of a body made from a nonallergenic material insoluble in larcimal fluids and containing a known quantity of therapeutic medication in a particular concentration. Preferably, the material from which the body is formed is a polymeric material through which the medication diffuses into the lacrimal fluids of the eye for uniform dispersion over the eye and distribution into adjacent regions.

It is an important feature of the present invention that the body have a generally annular shape with a size sufficient to allow placement of the delivery vehicle on a less sensitive area of the eye in circumscribing relationship with the corneal-scleral junction without intruding upon this more sensitive junction. The body extends over the surface of the eyeball away from the junction into the upper and lower conjunctival sacs under the upper and lower eyelids respectively. The eyelids and eye curvatures aid in retaining the delivery vehicle in place and thus supplement the capillary action generated by the lacrimal film between the delivery vehicle and the eyeball.

By sizing the body so that it circumscribes the corneal-scleral junction, the cornea is exposed in a natural manner. More importantly, the foreign-body awareness and retention problems experienced with the prior art inserts are reduced since the insert of the present invention is held in place by the eyelids and the compound curvatures of the eyeball in the region around the corneal-scleral junction.

BRIEF DESCRIPTION OF THE DRAWINGS

FIG. 1 is a perspective view illustrating the general frustospherical, annular configuration of the delivery vehicle of the present invention.

FIG. 2 is a frontal view of the human eye showing placement of the delivery vehicle in practice.

FIG. 3 is a sectional view of the human eye showing the delivery vehicle extending into the conjunctival sacs behind the upper and lower eyelids.

FIG. 4 is an enlarged sectional view of the eye and the delivery vehicle in the conjunctival sac behind the upper eyelid.

DESCRIPTION OF THE PREFERRED EMBODIMENTS

FIG. 1 illustrates the ophthalmic delivery vehicle of the present invention in a preferred embodiment. The delivery vehicle is inserted in the eye to dispense medication at a controlled rate for an extended period of time. For example, the delivery vehicle may be used to treat chronic disorders such as glaucoma by continuously dispensing a drug such as pilocarpine at a controlled rate for a period up to a week without replacement.

The vehicle, generally designated 10, is comprised of a body 12 formed from a nonallergenic material which is insoluble in lacrimal or tear fluids. A quantity of therapeutic medication is confined within the body so that it may be diffused through the surface of the body into the lacrimal fluids when the body is placed on the surface of the eyeball. The medication may be contained in a single-compartment reservoir within the body or be distributed in a finely divided manner in a porous material defining multiple interconnected reservoirs. By way of example, the material forming the body may be an imperforate polymeric material such as described in U.S. Pat. No. 3,618,604 referenced above or a microporous polymeric material in which the pores are filled with a liquid or gel medium for controlling the release rate of medication as described in U.S. Pat. No. 3,828,777 also referenced above. For a more detailed description of such materials and their structures, reference is made to the cited patents.

As shown in FIG. 1, the body 12 has a generally annular shape. The walls of the body have a slight spherical curvature so that the body resembles the frustum of a sphere defined between two parallel planes perpendicular to the polar axis 14 of the sphere. Such a frustospherical, annular shape has a polar marginal edge 16 at the front or anterior portion of the body and an equatorial marginal edge 18 at the rear or posterior edge of the body. The diameter of the annular body is smallest at the polar marginal edge 16 and is largest at the equatorial marginal edge 18. The diameters and curvature of the body are selected to allow the body to be placed in the eye as shown in FIGS. 2-4.

To more clearly understand the invention, a brief description of the anatomy of the eye is provided in connection with FIGS. 2-4. The eye fits in a cavity of the skull known as the orbit and is exposed at the anterior portion by the palpebral opening or fissure defined by the upper eyelid 20 and lower eyelid 22. The globe 24 or eyeball connects at the posterior with the optic nerve 26 and is comprised of two merged, generally spherical sections, the anterior section being defined as the cornea 28 which is transparent and the posterior section being defined as the sclera 30 which is white and more commonly referred to as the white of the eye. The eye muscles 32 and 34 are attached to the sclera for moving the eye in its orbital socket.

The pupil 36 of the eye is an opening on the optical axis and is defined by the iris 38 or colored portion of the eye situated posteriorly of and visible through the transparent cornea 28.

As shown in FIGS. 3 and 4, the cornea 28 has a much smaller radius of curvature than the sclera 30. In actuality, neither the cornea nor the sclera are truly spherical but tend to flatten slightly as the distance from the optical axis increases. The curvature of the cornea differs from person to person, and hence is difficult to utilize as an interface with delivery vehicles such as soft contact lenses which are placed directly on the cornea.

The junction of the sclera 30 and cornea 28 is identified as the limbus 40 and can be seen in the eye at the point where the white sclera joins the transparent cornea. The limbus, accordingly, defines the outer limit of the cornea which contains a high concentration of nerve endings serving to protect the cornea from dryness and injury from foreign objects. It is this corneal-scleral junction that identifies the region in which ophthalmic delivery vehicles should not intrude; otherwise the natural protective systems of the eye attempt to work the delivery vehicle out of the eye.

The conjunctiva 42 is a thin mucous membrane that connects the inner side of the eyelids to the eyeball in the vicinity of the corneal-scleral junction or limbus 40. As seen in FIG. 4, the conjunctiva is a folded membrane having a palpebral portion 44 that connects with the margins of the eyelids and extends in the posterior direction to a fold or fornix 46 and a bulbar portion 48 which extends from the fornix in the anterior direction over the eyeball where it merges with the sclera and the cornea at the limbus 40. The conjunctival sac thus forms a circular cul-de-sac known as the conjunctiva 42 which surrounds the eyeball and prevents foreign objects from migrating rearwardly under the eyelids to areas within the orbit behind the eyeball. The conjunctiva also serves as a small reservoir for lacrimal fluids which are wiped across the cornea by blinking the eyelids as needed to prevent corneal dryness. In the presence of irritations in the eye and the secretion of excess lacrimal fluids, the conjunctival sac fills with fluids and overflows to form tears, initially at the nasal corner of the eyelids.

In accordance with the present invention, the frustospherical delivery vehicle 10 is positioned on the globe of the eye coaxially of the optical axis and is sized so that it circumscribes the corneal-scleral junction 40 without intruding upon the junction. Thus, as illustrated in FIGS. 2 and 4, the polar marginal edge 16 of the body 12 has a diameter slightly larger than the diameter of the cornea 28. It is also common for the corneal-scleral junction to be flattened at the top and bottom edges so that it has a slightly elliptical shape with, for example, a horizontal dimension 12 mm and a vertical dimension of 11 mm. Preferably, the body 12 of the delivery vehicle 10 also has a slightly elliptical shape conforming to that of the junction. As a minimum, the inside diameter of the polar marginal edge should not be less than 11 mm to prevent intrusion onto the cornea 28.

The annular body 12 extends from the polar marginal edge 16 over the eyeball in the posterior direction with the upper and lower portions projecting into the conjunctival sacs behind the upper and lower eyelids 20 and 22. The curvature on the inner surface of the body between the marginal edges 16 and 18 is preferably matched with the curvature of the sclera in the region adjacent the limbus 40 so that the body lies flat on the bulbar portion 48 of the conjunctiva and remains in place due to the curvature and the capillary action developed by the film of lacrimal fluid on the eye and in the conjunctival sacs. The eyelids 20 and 22 overlie the exterior surface of the body 12 as shown most clearly in FIGS. 3 and 4 and develop additional forces for holding the body in place coaxially of the cornea 28. The degree to which the body 12 extends posteriorly behind the eyelids 20 and 22 depends partly upon the amount of semipermeable surface area needed to dispense medication in the eye. If the polar marginal edge 16 is spaced, for example, 1 mm from the cornea 28, then the diameter of the equatorial marginal edge 18 may be smaller than the corresponding diameter of a body which has the polar marginal edge 16 2 mm from the cornea, assuming the same dose rate is desired. It is contemplated, that the width of the annular body measured from the polar marginal edge to the equatorial marginal edge will in most cases be not more than 4 mm and will lie generally in the range of 2-4 mm. The thickness of the body from the interior surface contacting the bulbar portion 48 of the conjunctiva to the exterior surface contacting the palpebral portion 44 may also vary between 0.1 mm and 1 mm with a nominal dimension being 0.2 mm.

Thus, with the annular delivery vehicle 10 in the eye, the lacrimal fluid and the blinking action of the eyelids carry medication diffused through the surface of the body over the eyeball and allow the medication to operate in the eye and surrounding regions. The body 12 is held firmly in position by capillary forces and the curvatures of the sclera in the region of the limbus 40. Thus, movement of the eyeball does not have a tendency to dislodge the body. The body is sized to remain outside of the highly sensitive corneal region to prevent irritation and also fully exposes the cornea in a natural manner to the eyelids and lacrimal fluids. Accordingly, the foreign-body awareness problem and the retention problems of the prior art devices are minimized, and with the cornea fully exposed, drying or oxygen depletion which occurs after prolonged wearing of a soft contact lens is avoided entirely.

While the delivery vehicle 10 has been described in a preferred embodiment, it should be understood that numerous variations in its structure can be had without departing from the spirit of the invention. For example, the body may also be constructed with bioerodable material as defined in U.S. Pat. No. 3,867,519 so that removal of the delivery vehicle from the eye after the medication has been expended is not necessary. The body may also have a composite structure with a drug-impregnated matrix and an insoluble polymeric membrane as the outer skin as defined in U.S. Pat. No. 3,854,480. Accordingly, the present invention has been described in a preferred embodiment by way of illustration rather than limitation.

I claim:

1. A method for delivering therapeutic medications directly to the cornea of a pre-selected eye comfortably and efficiently, comprising the steps of:
   A. forming a substantially frusto-spherical, continuous, annular-shaped body from non-allergenic material, insoluble in lacrimal fluids with
      a. the edges of said body being defined by two concentric circles, and
      b. the annular eye-contacting surface between said concentric circles substantially conforming to the overall curvature of the sclera of the pre-selected eye,
   B. forming the inside, edge-defining concentric circle of said annular-shaped body with a diameter slightly larger than the diameter of the corneal-scleral junction of the pre-selected eye;
   C. diffusing therapeutic medication throughout the annular body for retension therein and subsequent diffusion to the cornea of the pre-selected eye; and
   D. fitting the medication-containing annular body to the pre-selected eye with the inside circular edge thereof peripherally surrounding the corneal-scleral junction in close, juxtaposed spaced relationship, without intruding therein,
whereby an ophthalmic delivery vehicle is attained which assures delivery of medication directly to the cornea of the eye, effectively and efficiently, while also being highly comfortable to the wearer.

2. The method defined in claim 1, comprising the additional step of
   E. forming the annular body with a width sufficient to contain the medication, provided said outside, edge-defining concentric circle comprises a diameter less than the arcuate distance between the upper and lower conjunctival sacs of the pre-selected eye.

3. A method for delivering therapeutic medications directly to the cornea of a pre-selected eye comfortably and efficiently, comprising the steps of:
   A. forming a substantially frusto-spherical, continuous, annular-shaped body from non-allergenic material, insoluble in lacrimal fluids with
      a. the edges of said body being defined by two concentric circles, and
      b. the annular eye-contacting surface between said concentric circles substantially conforming to the overall curvature of the sclera of the pre-selected eye,
   B. forming the inside, edge-defining concentric circle of said annular-shaped body with a diameter substantially coinciding with the diameter of the corneal-scleral junction of the pre-selected eye;
   C. forming the outside, edge-defining concentric circle of said annular-shaped body with a diameter less than the arcuate distance between the upper and lower conjunctival sacs;
   D. diffusing therapeutic medication throughout the annual body for retension therein and subsequent diffusion to the cornea of the pre-selected eye; and
   E. fitting the medication-containing annular body to the pre-selected eye with the inside circular edge thereof peripherally surrounding the corneal-scleral junction in close, juxtaposed spaced relationship, without intruding therein,
whereby an ophthalmic delivery vehicle is attained which assures delivery of medication directly to the cornea of the eye, effectively and efficiently, while also being highly comfortable to the wearer.

* * * * *